(12) United States Patent
Miller

(10) Patent No.: US 8,728,078 B2
(45) Date of Patent: May 20, 2014

(54) CLAMPING ASSEMBLY WITH LINKS

(75) Inventor: Stephen T. Miller, Scotts Valley, CA (US)

(73) Assignee: Zimmer, Inc., Warsaw, IN (US)

( * ) Notice: Subject to any disclaimer, the term of this patent is extended or adjusted under 35 U.S.C. 154(b) by 165 days.

(21) Appl. No.: 13/289,214

(22) Filed: Nov. 4, 2011

(65) Prior Publication Data

US 2012/0289959 A1 Nov. 15, 2012

Related U.S. Application Data

(60) Provisional application No. 61/410,248, filed on Nov. 4, 2010.

(51) Int. Cl.
*A61B 17/00* (2006.01)
*A61F 4/00* (2006.01)
*A61F 5/04* (2006.01)

(52) U.S. Cl.
USPC ............................................ 606/59; 606/324

(58) Field of Classification Search
USPC ............. 606/54–59, 246, 250–253, 260, 264, 606/276–279, 324; 403/385, 389, 391, 396, 403/398, 400
See application file for complete search history.

(56) References Cited

U.S. PATENT DOCUMENTS

| | | |
|---|---|---|
| 1,706,215 A | 3/1929 | Davidson |
| 2,705,603 A | 4/1955 | Bitz et al. |
| 3,044,512 A | 7/1962 | Jones |
| 3,154,331 A | 10/1964 | Engelhardt |
| 3,373,465 A | 3/1968 | Johnson et al. |
| 3,406,987 A | 10/1968 | Hunder et al. |
| 4,037,978 A | 7/1977 | Connelly |
| 4,115,966 A | 9/1978 | DeLee |
| 4,312,488 A | 1/1982 | Pierron |
| 4,388,747 A | 6/1983 | Plummer |
| 4,483,334 A | 11/1984 | Murray |
| 4,620,533 A | 11/1986 | Mears |
| 4,653,481 A | 3/1987 | Howland et al. |

(Continued)

FOREIGN PATENT DOCUMENTS

| | | |
|---|---|---|
| DE | 2430234 | 1/1975 |
| EP | 1820461 | 8/2007 |

(Continued)

OTHER PUBLICATIONS

European Patent Office, International Search Report and Written Opinion mailed Mar. 28, 2012, Application No. PCT/US2011/963985, 10 pages.

(Continued)

*Primary Examiner* — Mary Hoffman
*Assistant Examiner* — Michelle C Eckman
(74) *Attorney, Agent, or Firm* — Schwegman Lundberg & Woessner, P.A.

(57) ABSTRACT

An external fixation system includes a clamp system configured to capture a fixation element. The clamp system has a first and a second jaw and a first and a second link attached to the first and second jaws that are configured to control the motion of the jaws. The links are arranged such that, when the first and second jaws are moved to a closed position, the action of trying to open the jaws is resisted by the position of the links, and to open the jaws, the links must be actuated.

21 Claims, 13 Drawing Sheets

(56) References Cited

U.S. PATENT DOCUMENTS

| | | | |
|---|---|---|---|
| 4,662,365 | A | 5/1987 | Gotzen et al. |
| 4,700,437 | A | 10/1987 | Hoshino |
| D295,725 | S | 5/1988 | Shioda |
| 4,817,897 | A | 4/1989 | Kreusel |
| 5,259,690 | A * | 11/1993 | Legge .......................... 403/385 |
| 5,312,405 | A | 5/1994 | Korotko et al. |
| 5,427,465 | A | 6/1995 | Sato |
| 5,662,648 | A | 9/1997 | Faccioli et al. |
| 5,683,389 | A | 11/1997 | Orsak |
| 5,709,681 | A | 1/1998 | Pennig |
| 5,727,899 | A | 3/1998 | Dobrovolny |
| 5,741,252 | A | 4/1998 | Mazzio et al. |
| 5,746,741 | A | 5/1998 | Kraus et al. |
| 5,752,954 | A | 5/1998 | Mata et al. |
| 5,800,548 | A | 9/1998 | Martin et al. |
| 5,827,282 | A | 10/1998 | Pennig |
| 5,860,728 | A | 1/1999 | Maglica |
| 5,891,144 | A | 4/1999 | Mata et al. |
| 5,976,141 | A | 11/1999 | Haag et al. |
| 6,022,348 | A | 2/2000 | Spitzer |
| 6,080,153 | A | 6/2000 | Mata et al. |
| 6,102,911 | A | 8/2000 | Faccioli et al. |
| 6,217,577 | B1 | 4/2001 | Hofmann |
| 6,264,396 | B1 | 7/2001 | Dobrovolny |
| 6,277,069 | B1 | 8/2001 | Gray |
| 6,376,775 | B1 | 4/2002 | Leijon et al. |
| 6,386,786 | B1 | 5/2002 | Perlman et al. |
| 6,409,729 | B1 | 6/2002 | Martinelli |
| 6,500,177 | B1 | 12/2002 | Martinelli et al. |
| 6,637,082 | B1 | 10/2003 | Chang |
| 6,652,523 | B1 | 11/2003 | Evrard et al. |
| 6,702,814 | B2 | 3/2004 | Walulik et al. |
| 6,716,212 | B1 | 4/2004 | Pickens |
| 6,736,775 | B2 | 5/2004 | Phillips |
| 6,887,197 | B2 | 5/2005 | Phillips |
| 7,004,943 | B2 | 2/2006 | Ferrante et al. |
| 7,048,735 | B2 | 5/2006 | Ferrante et al. |
| 7,241,071 | B2 | 7/2007 | Carraher et al. |
| 7,241,074 | B2 | 7/2007 | Thomket et al. |
| 7,261,713 | B2 | 8/2007 | Langmaid et al. |
| 7,314,331 | B1 | 1/2008 | Koros et al. |
| 7,320,556 | B2 | 1/2008 | Vagn-Erik |
| 7,473,223 | B2 | 1/2009 | Fetzer |
| 7,491,008 | B2 | 2/2009 | Thomke et al. |
| 7,527,626 | B2 | 5/2009 | Lutz et al. |
| 7,562,855 | B2 | 7/2009 | Oetlinger |
| 7,588,537 | B2 | 9/2009 | Bass |
| 7,708,736 | B2 | 5/2010 | Mullaney |
| 7,744,632 | B2 | 6/2010 | Usher |
| 7,931,650 | B2 | 4/2011 | Winquist et al. |
| 7,938,829 | B2 | 5/2011 | Mullaney |
| 2001/0004432 | A1 | 6/2001 | Pfister |
| 2002/0037193 | A1 | 3/2002 | Gibbons et al. |
| 2002/0042613 | A1 | 4/2002 | Mata |
| 2002/0061225 | A1 | 5/2002 | Boucher et al. |
| 2002/0165543 | A1 | 11/2002 | Winquist et al. |
| 2003/0149429 | A1 | 8/2003 | Ferranet et al. |
| 2005/0113831 | A1 | 5/2005 | Franck et al. |
| 2005/0119656 | A1 | 6/2005 | Ferrante et al. |
| 2006/0017566 | A1 | 1/2006 | Gauvreau et al. |
| 2006/0039750 | A1 | 2/2006 | Thomke et al. |
| 2006/0229602 | A1 | 10/2006 | Olsen |
| 2006/0229603 | A1 | 10/2006 | Olsen |
| 2006/0255521 | A1 | 11/2006 | Brunner et al. |
| 2006/0271045 | A1 | 11/2006 | Hubbard et al. |
| 2006/0287652 | A1 | 12/2006 | Lessig et al. |
| 2007/0038217 | A1 | 2/2007 | Brown et al. |
| 2007/0049932 | A1 | 3/2007 | Richelsoph et al. |
| 2007/0198012 | A1 | 8/2007 | Thomke et al. |
| 2007/0293860 | A1 | 12/2007 | Oesch |
| 2008/0065068 | A1 | 3/2008 | Thomket et al. |
| 2008/0215053 | A1 | 9/2008 | Thomke et al. |
| 2009/0036891 | A1 | 2/2009 | Brown et al. |
| 2009/0088751 | A1 * | 4/2009 | Mullaney .......................... 606/59 |
| 2009/0299368 | A1 | 12/2009 | Bauer |
| 2011/0098706 | A1 | 4/2011 | Mullaney |
| 2011/0098707 | A1 | 4/2011 | Mullaney |
| 2011/0172663 | A1 | 7/2011 | Mullaney |
| 2012/0004659 | A1 | 1/2012 | Miller et al. |
| 2012/0089142 | A1 | 4/2012 | Mullaney et al. |
| 2012/0095462 | A1 | 4/2012 | Miller |

FOREIGN PATENT DOCUMENTS

| | | |
|---|---|---|
| EP | 2294994 | 3/2011 |
| WO | WO-89/05126 | 6/1989 |
| WO | WO-90/11055 | 10/1990 |
| WO | WO-92/12683 | 8/1992 |
| WO | WO-98/51227 | 11/1998 |
| WO | WO-99/25264 | 5/1999 |
| WO | WO-03065911 | 8/2003 |
| WO | WO-2009/004347 | 1/2009 |
| WO | WO-2012061692 A1 | 5/2012 |

OTHER PUBLICATIONS

European Patent Office, International Search Report and Written Opinion mailed Apr. 10, 2012, Application No. PCT/US2011/063976, 8 pages.

European Patent Office, International Search Report and Written Opinion mailed Jan. 9, 2012, Application No. PCT/US2011/055907, 9 pages.

International Searching Authority/European Patent Office, "Notification of Transmittal of the International Search Report and the Written Opinion of the International Searching Authority, or the Declaration," for PCT/US2011059303, mailed Mar. 20, 2012, 13 pages.

Swiss Patent Office, Application No. 03 891/90-6, titled "Fixateur externe," Applicant—Jaquet Orthopedie S.A., filed Dec. 16, 1991, 34 pages.

European Patent Office, International Search Report and Written Opinion dated Oct. 13, 2011, Application No. PCT/US2011/042813, 11 pages.

PCT/ISA-US Office, International Search Report and Written Opinion dated Dec. 2, 2008, Application No. PCT/US08/77800, 11 pages.

"International Application Serial No. PCT/US2011/059303, International Preliminary Report on Patentability mailed May 7, 2013", 9 pgs.

* cited by examiner

CLAMPING ASSEMBLY WITH LINKS

PRIORITY

This application claims priority to and the benefit of the filing date of U.S. Provisional Patent Application No. 61/410,248, filed Nov. 4, 2010, which is incorporated herein by reference.

FIELD OF THE INVENTION

This application is directed to a clamping system for an external fixation system.

BACKGROUND

External fixation systems are used to stabilize fractured bones or secure bones after corrective surgery. They are usually made up of structural members held together by clamps, all assembled by the surgeon during surgery. The clamps are placed on bone pins and are attached to bars, creating a frame to hold the bones in particular relationships. Typically, the external fixation frame is assembled in the configuration the surgeon desires, then the fracture is reduced and the clamps are tightened. Some conventional clamps have to be tightened partially to provisionally lock the bone pin or bar into the clamp. Others require insertion of a fixation element against a spring force possibly making insertion more difficult than necessary.

The present disclosure overcomes one or more of the deficiencies in the prior art.

SUMMARY

This disclosure is directed to a clamping assembly that is structurally arranged to grasp a bone pin or bar and structurally arranged to hold onto that fixation element against force trying to remove that element from the clamping assembly.

In one exemplary aspect, the present disclosure is directed to a clamp assembly for an external fixation system. The clamp assembly may include a first jaw and a second jaw, the second jaw having an inner surface facing the first jaw. The first and second jaws together form a passage for receiving a first fixation element of the external fixation system. A first link is attached to the first jaw, and a second link is attached to the second jaw. The first and second links are configured to control the relative motion of the first and second jaws and are arranged such that, when the first and second jaws are moved to a closed position, the first and second links resist separation of the jaws.

In one aspect, the first and second links are pivotable between a first position and a second position, with the first and second links being configured in a manner that the first and second jaws open when the first and second links are disposed in the first position. In another aspect, the clamp assembly includes a biasing element separating the first and second clamps. The first clamp may be arranged so that the biasing element biases the clamp to an open position when the first and second links are disposed in a first position. In one aspect, the first clamp is arranged so that the biasing element biases the clamp to a closed position when the first and second links are disposed in a second position.

In another exemplary aspect, the present disclosure is directed to an external fixation system. The system includes a first fixation element and a second fixation element. It also includes a first clamp configured to capture the first fixation nt. The first clamp includes a first linkage comprising first and second links which may be actuated to open the first clamp. A second clamp is pivotable relative to the first clamp and configure to capture the second fixation element. The second clamp includes a second linkage comprising third and fourth links which may be actuated to open the second clamp.

In another exemplary aspect, the present disclosure is directed to a method of clamping a fixation rod in an external fixation clamp. The method includes inserting a fixation element into a passage formed between first and second jaws of a clamp, and pressing a link to pivot an upper jaw relative to a lower jaw. Pressing a link may include separating a portion of the first and second jaws apart via a linkage connecting the first and second jaws, moving the link beyond a neutral position, and allowing said portion of the first and second jaws to move toward each other to render the clamp in a closed position.

In another exemplary aspect, an external fixation system may include a plurality of rods, a plurality of pins, and first and second clamp systems. Each clamp system is configured to capture a rod or a pin. Each clamp system has a first and a second jaw and a first and a second link attached to the jaws and configured to control the motion of the jaws. The links are arranged such that, when the first and second jaws are moved to a closed position, the action of trying to open the jaws is resisted by the position of the links, and to open the jaws, the links must be actuated.

BRIEF DESCRIPTION OF THE DRAWINGS

Aspects of the present disclosure are best understood from the following detailed description when read with the accompanying figures.

DETAILED DESCRIPTION

Figure 1:
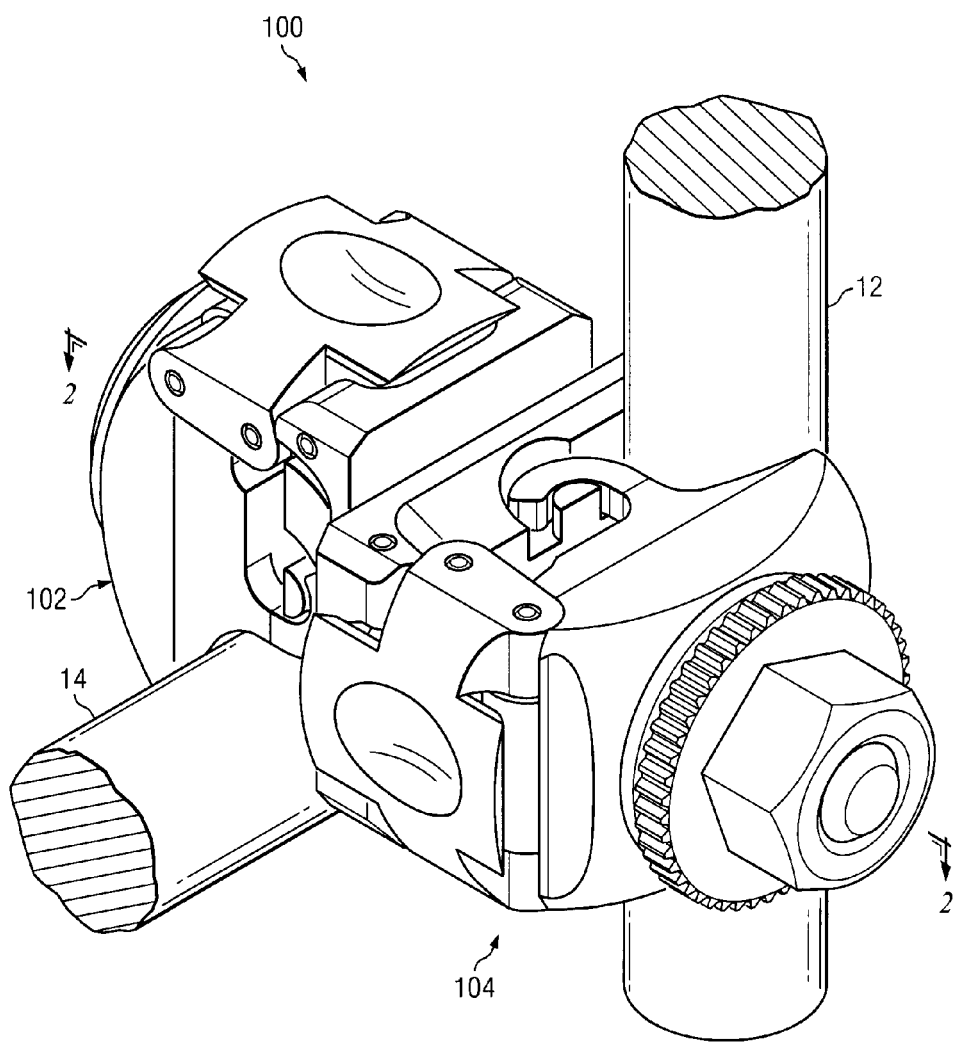
FIG. 1 is an isometric view of a portion of an external fixation system showing one exemplary embodiment of a clamping assembly clamped onto fixation bars.

It is to be understood that the following disclosure provides many different embodiments, or examples, for implementing different features of various embodiments. Specific examples of components and arrangements are described below to simplify the present disclosure. These are, of course, merely examples and are not intended to be limiting. In addition, the present disclosure may repeat reference numerals and/or letters in the various examples. This repetition is for the purpose of simplicity and clarity and does not in itself dictate a relationship between the various embodiments and/or configurations discussed.

The external fixation system disclosed herein includes a clamping device having one or more clamps, arranged to receive and secure fixation rods or bars (or other fixation elements) and/or pins (or other fixation elements) that extend into and secure patient tissue. These clamps, however, may be arranged to open to a first condition wider than the width of the fixation element to be received, and configured to close or clamp onto the fixation element. A user can lock the clamp in the closed position by pressing a unique linking system that secures the fixation element within the clamp.

FIG. 1 shows an exemplary external fixation system 10 including rigid bars 12, 14 and a clamping device 100. Although this disclosure references bars 12, 14 and later references pins, it should be understood that any fixation element may be used, including bone pins, wires, rings, struts, bars, rods, or other structural members. In the example in FIG. 1, each bar 12, 14 is received into the clamping device 100 by inserting it between facing jaws of a clamp of the clamping device 100 as is described further below, to establish the external fixation framework for bone stabilization. The bars 12, 14 may be held in the clamp in a provisionally locked position. In this position, the respective clamp can be rotated about the fixation element and may be axially displaced along the fixation element. In addition, at least one of the clamps may rotate about a longitudinal axis of the clamping device 100 while the jaws maintain the fixation element in the clamp. Additional bar-to-bar fixation clamps and/or bar-to-pin fixation clamps may be added to expand and create an external fixation frame as required. Once properly created, the frame may be locked by changing the clamp from a provisionally locked condition to the fully locked condition.

Figure 2:
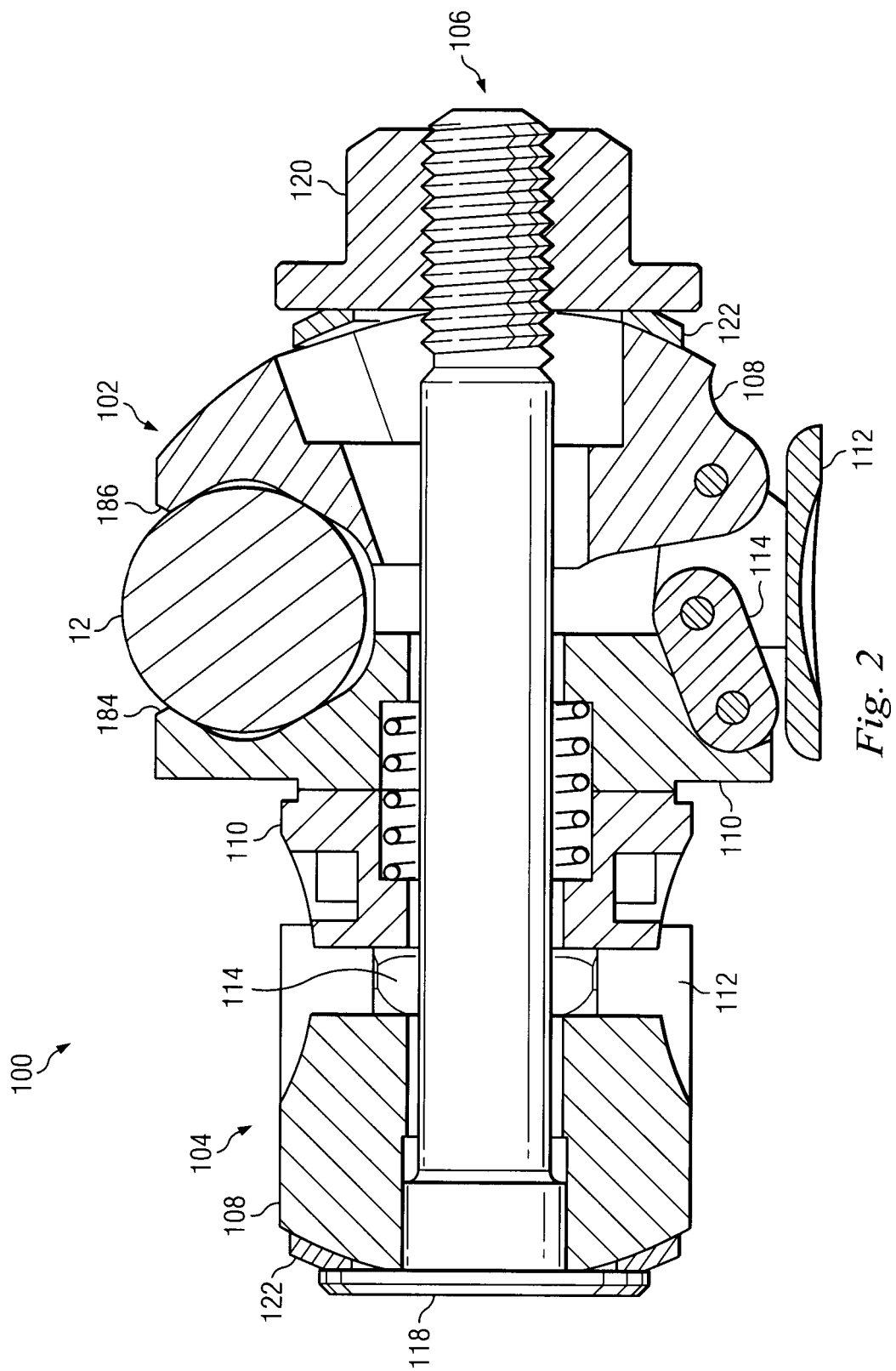
FIG. 2 is a section view of the exemplary clamp assembly of FIG. 1 taken through lines 2-2, and showing only one of the fixation bars.
Figure 3:
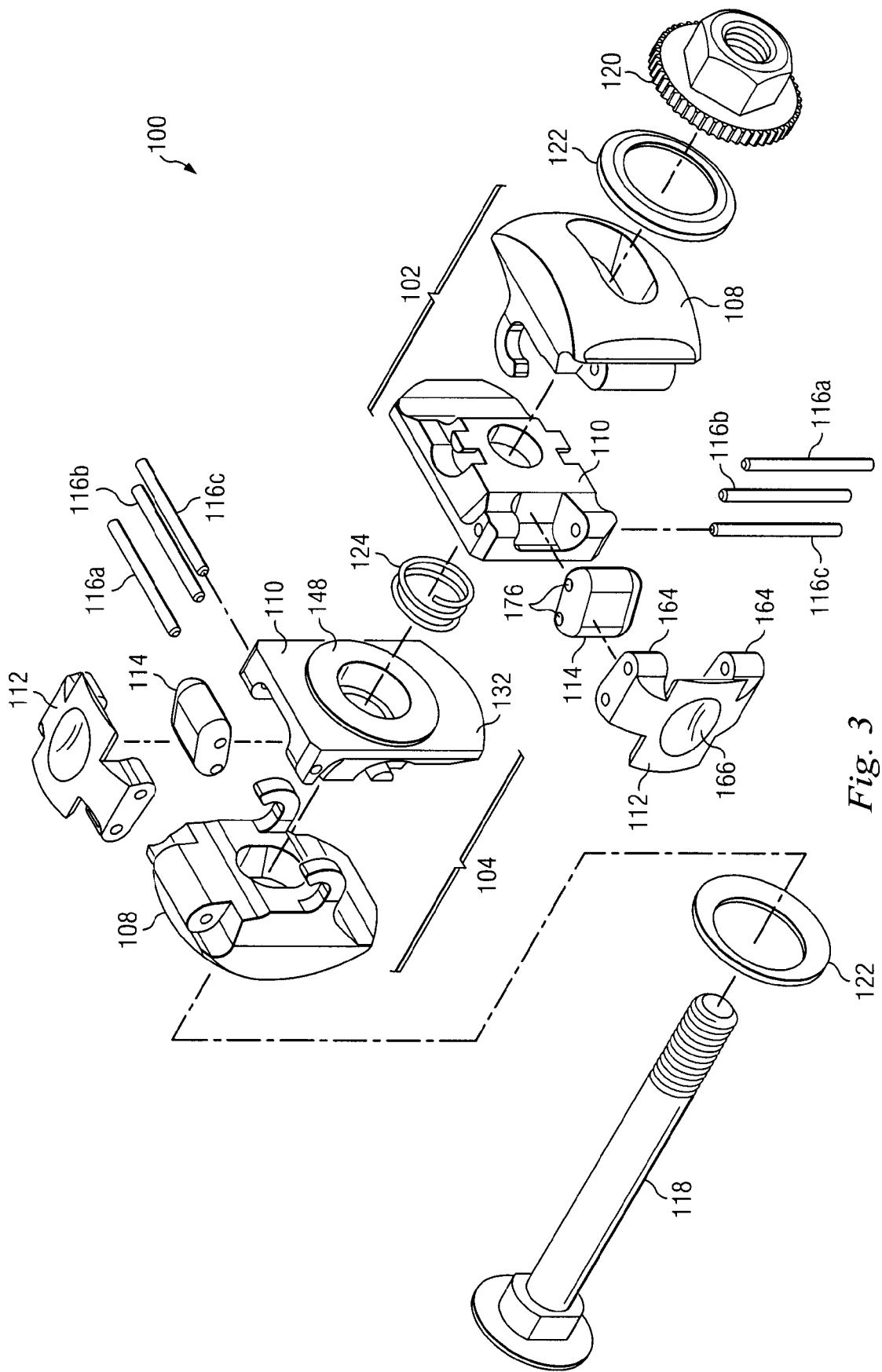
FIG. 3 is an illustration of an exploded view of the exemplary clamp assembly of FIG. 1.

FIGS. 2 and 3 show additional details of an embodiment of the clamping device 100 according to one exemplary aspect of the present disclosure. Some like elements may be labeled with a suffix or separate reference number for clarity.

The exemplary clamping device 100 includes a clamp 102, a clamp 104, and a locking assembly 106. Each clamp 102, 104 independently receives and secures a bar, pin or other fixation element. In this example, each clamp is configured as a bar clamp. Other embodiments of the clamping device 100 include a bar clamp and a pin clamp, while others include two pin clamps. Yet other embodiments include only a single clamp on one end, with a multi-clamp set or other arrangement on the other end.

Each clamp 102, 104 of the clamping device 100 provides multiple degrees of freedom, including a roll axis and a yaw axis. The roll axis is the axis of a fixation element within one of the clamps and about which the clamping device 100 may rotate when the clamp is only provisionally locked. The yaw axis is defined by a stud (described below) and about which one of the clamps 102, 104 can rotate relative to the other.

FIGS. 2 and 3 respectively show a cross-sectional view and an exploded view of the clamping device 100. Referring to FIGS. 1-3, the clamps 102, 104 each include an outer jaw 108, an inner jaw 110, a block 112, a link 114, and three axles 116a-116c. The locking assembly 106 includes a stud shown as a bolt 118 and a locking member shown as a nut 120. In addition to these elements of the clamps 102, 104 and the locking assembly 106, the clamping device 100 includes a washer 122 disposed adjacent each outer jaw 108 and includes a biasing member 124 disposed between the inner jaws 110.

The clamps 102, 104 open for reception of a fixation element, such as the fixation rod 12 in FIG. 1. These cooperate with the block 112 and the link 114 to apply loading that clamps the fixation element in a passage between the inner and outer jaws.

Figure 4:
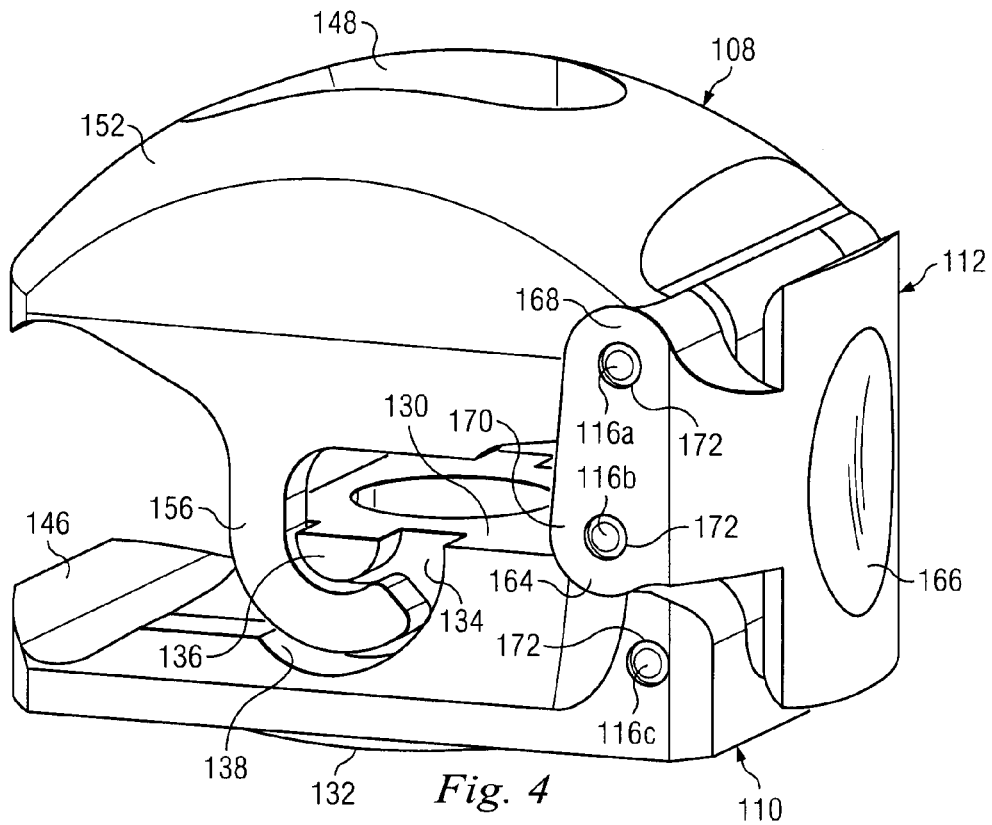
FIG. 4 is an illustration of a perspective view of a clamp of the exemplary clamping assembly of FIG. 1.
Figure 5:
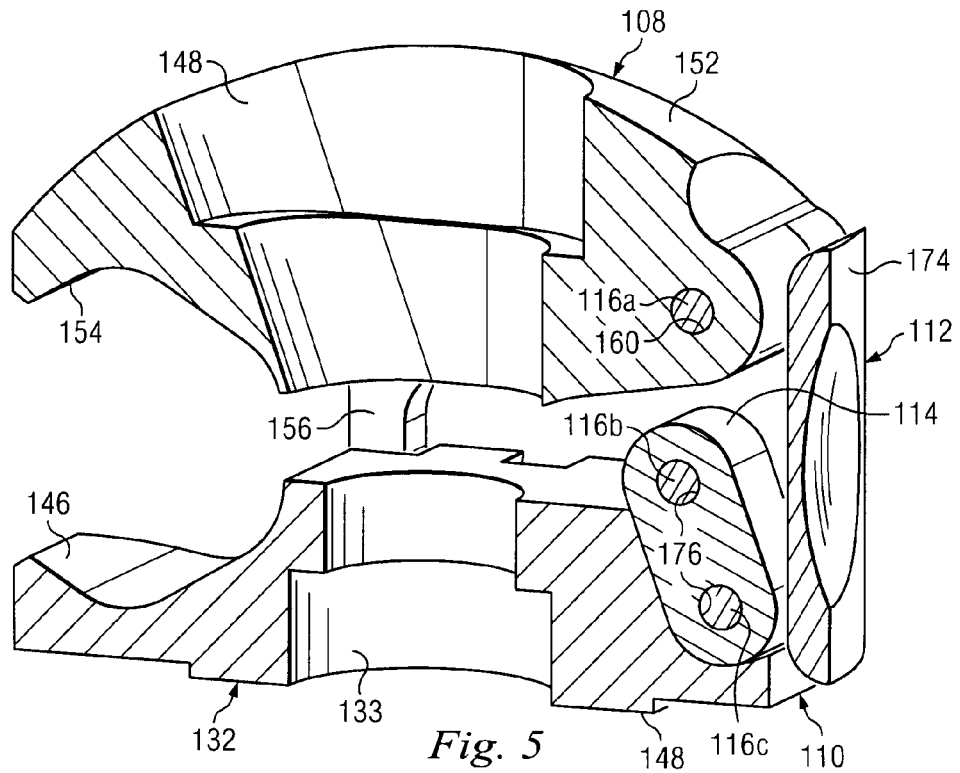
FIG. 5 is an illustration of a cross-sectional view of the clamp of FIG. 4.
Figure 6:
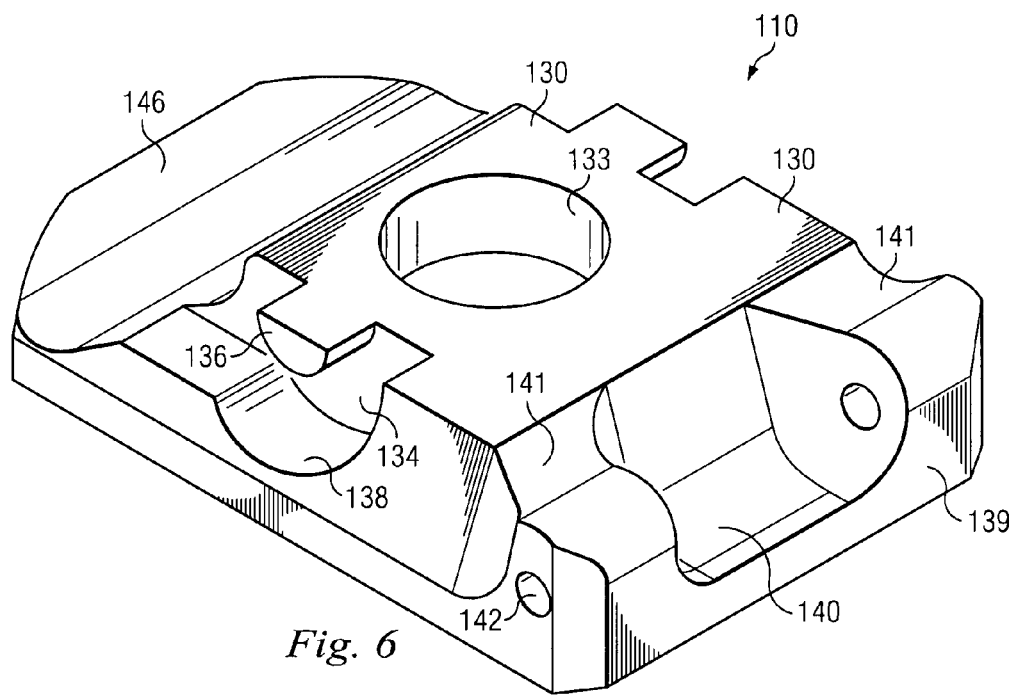
FIG. 6 is an illustration of a perspective view of an inner jaw of the clamp of FIG. 4.

FIGS. 4 and 5 shows the clamp 102 in greater detail. FIG. 4 shows a perspective view and FIG. 5 shows a cross-sectional view of the clamp 102. FIG. 6 shows another view of the inner jaw 110 separate from and independent of other elements of the clamp 102.

Referring to these Figures, the inner jaw 110 cooperates with the outer jaw 108 to clamp onto and secure a fixation element. The inner jaw 110 includes an inner clamp face 130 that faces toward the outer jaw 108 and includes an outer clamp face 132 (see FIG. 3) that faces and interfaces with the clamp 104 (FIG. 3). A central bore 133 extends from the inner clamp face 130 to the outer clamp face 132 and is sized to receive the bolt 118. The central bore 133 includes a spring recess configured to receive the biasing member 124. In addition, the inner jaw 110 includes a track 134 and a connector portion shown as a boss 136 formed on each lateral side. The boss 136 in this embodiment is formed as a half-cylinder projecting laterally from the inner jaw 110. Here, the boss 136 includes an axis formed by the cylindrical shape that is coincident with the plane of the inner clamp face 130. The track 134 is formed between the boss 136 and a cylindrical surface 138 concentric with the cylindrical surface of the boss 136.

The inner clamp face 130 includes a gripping surface portion 146 configured to interface with a fixation element such as a rod 12 from FIG. 1. In this example, the gripping surface portion 146 is a lateral recess. Although shown as smooth, the gripping surface portion may include a plurality of transverse teeth formed therein extending from one lateral side to the other that may interface or engage with a fixation element that is held between the inner and outer jaws 110, 108. The gripping surface portion 154 may be formed with a rounded bottom portion, flats, faces, some other engaging surface, or some combination of these.

The outer clamp face 132 includes a clamp interfacing portion 148 that selectively interfaces with the opposing clamp to restrict relative rotation when the clamping device 100 is in a fully locked condition. In one embodiment, the clamp interfacing portion 148 includes interdigitating portions. In some examples, these include poker-chip type surfaces, such as radially extending splines configured to interdigitate with the corresponding splines on the opposing clamp. In some examples, in place of the splines, the clamp interfacing portion 148 includes knurling, a roughened surface or other friction inducing features to enable the inner jaw 110 and the opposing interfacing surface of the opposing clamp to be selectively secured relative to each other. Some embodiments have smooth surfaces that frictionally engage under load to provide for and prevent selective relative rotation.

A rear portion 139 of the inner jaw 110 includes a seat 140 shaped to receive the link 114. The seat 140 is formed in the rear surface and in the inner clamp face 130 of the inner jaw 110. As seen in FIGS. 5 and 6, it includes a sloping surface and a curved basin at the bottom that matches the profile of the link 114. A block seat 141 is disposed adjacent the seat 140 and is configured to receive ends of a portion of the block 112 described below.

An axle hole 142 passes through lateral sides of the inner jaw 110 and into the seat 140. One of the axles 116c extends through the hole 142 and into the link 114, pivotably connecting the link 114 and the inner jaw 110.

Figure 7:
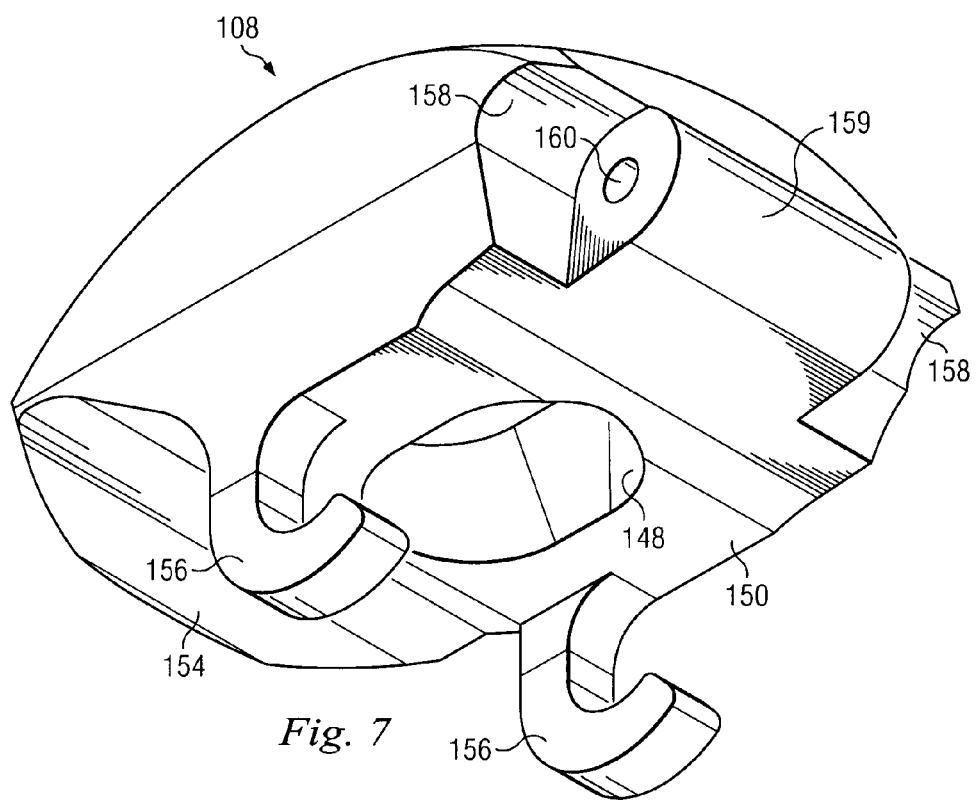
FIG. 7 is an illustration of a perspective view of an outer jaw of the clamp of FIG. 4.

FIG. 7 shows the outer jaw 108 in greater detail. With reference to FIG. 7, and with reference to FIGS. 4 and 5, the outer jaw 108 includes a central bore 148, an inner clamp face 150, and an outer clamp face 152. The inner clamp face 150 includes a fixation element-receiving gripping surface portion 154 formed as a transverse groove and extending from one lateral side to another. It is shaped to cooperate with the inner jaw 126 to receive and secure a bar, pin or other fixation element in place between the inner and outer jaws. Like the gripping surface portion 146, the gripping surface portion 154 may be formed with a rounded bottom portion, flats, faces, some other engaging surface, or some combination of these. The gripping surfaced portion 146 and the gripping surface portion 154 form a passage therebetween for receiving and capturing a fixation element, such as a spinal rod, a bone pin, or other fixation element.

Connector portions extend from the inner clamp face 150. These connector portions are arranged to interface with the bosses 136 on the inner jaw 110. In this example, the connector portions are J-shaped hooks 156 that extend into the track 134 and about the bosses 136. These hooks 156 enable the outer jaw 108 to pivot about the bosses 136 on the inner jaw 110, including about the center of the J-shaped hook. In this case, since the bosses 136 are semi-cylindrically shaped having an axis coincident with the inner clamp face 130, the pivot axis substantially corresponds to the inner clamp face 130. The tracks 134 limit and guide the motion of the hooks 156, and the hook shape prevents undesired removal. In addition, the spacing of the track 134 and the length of the hook 156 maintain a desired spacing between the inner and outer jaws 110, 108.

The outer jaw 108 also includes lateral recesses 158 toward a rear portion 159 that receive and cooperate with the block 112. A hole 160 passes transversely through the outer jaw 108 and into the lateral recesses 158. The axle 116a may be received into the hole 160 and through the block 112 to connect the block 112 to the outer jaw 108.

The outer clamp face 152 in this example is a smooth spherically-shaped surface that is configured to pivot or slide next to the washer 122. In this example, the washer 122 has a smooth spherical surface that nests with the outer clamp face 152. However, other shapes are contemplated. The central bore 148 includes features that enable it to articulate relative to the bolt 118. As such, the central bore 148 is relatively oval shaped, with curved ends connected by parallel sides that allow the outer jaw 108 to displace within a plane relative to the bolt.

Returning to FIGS. 3 and 4, the block 112 includes two arm portions 164 connected by a back portion 166. As explained further below, the arm portions 164 are configured to cooperate with the inner jaw 110 and the outer jaw 108 to physically restrict or block the rear portions of the jaws from coming together, thereby restricting or blocking separation of the front ends of the jaws 108, 110. This can prevent undesirable removal of the fixation element. Accordingly, the arm portions 164 each include a first end 168 and a second end 170 configured to respectively fit within or seat on the block seat 141 on the inner jaw 110 and the lateral recesses 158 on the outer jaw 108. With the arm portions 164 within their seats 141, 158, they provide interference that prevents the jaws' rear portions 139, 159 from moving together and thereby prevents separation of the front end of the jaws. Sets of holes 172 extend through each of the ends 168, 170 of the arm portions 164. The sets of holes 172 in each arm portion 164 align with each other, such that a single axle 116 fits through each set of holes 170, although separate axles or other arrangements may be employed. The back portion 166 extends between and connects the arm portions 164. In this example, the back portion 166 includes tabs 174 that longitudinally extend in the direction of the arm portions 164. These tabs 174 form a plate configured to be pressed by a user's finger or thumb to secure the clamp 102 on a fixation element. As shown in FIG. 4, first ends 168 of the arm portions 164 are received into the lateral recesses 158 formed in the outer jaw 108, and the second ends 170 of the arm portions 164 are received into the block seats 141 in the inner jaw 110.

Although the block 112 may be disposed between the jaws 108, 110 in a manner that mechanically prevents the rear portions 139, 159 from moving towards each other as discussed above, other embodiments rely upon the arrangement of the links and the axles to restrict the rear portions 139, 159 from moving toward each other. For example, simply restricting the link 114 from swinging towards the center of the clamp 102 prevents the rear portion 159 of the outer jaw 108 from moving downward toward the rear portion 139 of the inner jaw 110. For example, the load may instead go through the axles. Since the axles 116 are relatively small pins, the recesses and the block seat in FIGS. 5-7 allow the load to be carried by the block 112 while reducing the chance of overstressing the axles.

The link 114 is a solid block configured to fit between the arm portions 164 of the block 112. Each end of the link 114 includes a hole 176 for receiving one of the axles 116. As can be seen in FIG. 5, the link 114 is configured to be received within the seat 140.

In the example shown, the inner jaw 110 is configured to receive the axle 116c through the hole 142. The link 114 has two holes 176, one of which also receives the axle 116c. The other hole 176 receives the similar axle 116b. This axle 116b is also received in a hole 172 in the block 112, pivotably connecting the link 114 and the block 112. The other end of the arm portion 164 of the block 112 receives the axle 116a, which is also received in the hole 160 in the outer jaw 108.

The hook 156 of the outer jaw 108 bears against the inner jaw 110. This hook 156 is also captured by the boss 136 of the inner jaw 110, preventing or limiting the distance that the outer jaw 108 can travel. When the tab 174 on the block 112 is pressed in towards the middle of the clamp 102, the outer jaw 108 rotates around the boss 136, and the outer jaw 108 closes on a fixation element between the jaws 108, 110. In this example, the hook 156 has a cross-sectional width smaller than a cross-sectional width of the track 134 so that the hook 156 can not only pivot about the boss 136, but the hook 156, and thus the outer jaw 108 as a whole, can also displace vertically relative to the inner jaw 110. As such, while the three axle pivot points are nearly fully constrained in this embodiment, the J-hook is sized to be smaller than the track 134 so the outer jaw 110 can lift up when the links are pushed over center (as described below with reference to FIG. 8C), and so the outer and inner jaws 108, 110 can be pushed together when tightening the nut 120.

The section view in FIG. 5 shows the holes 176 in the link 114 for receiving the axles 116b, 116c, and also shows the hole 160 in the outer jaw 108, for receiving axle 116a.

In the exemplary embodiment shown, the clamp 102 includes four cooperating components that act as links of a linkage—the inner jaw 110, the outer jaw 108, the link 114, and the block 112. These together, pivoting about the three axles 116 and about the pivot connection formed at the hook and boss, help control the response to user manipulation of the block 112, as manipulated by its back portion 166 or its tab 174.

Returning to FIGS. 2 and 3, the biasing member 124 biases the forward ends of the inner and outer jaws of each clamp 102, 104 apart from each other based on one position of the linkage and also biases the forward ends of inner and outer jaws of each clamp 102, 104 towards each other based on another position of the linkage. By biasing the forward ends of the jaws 108, 110 of each clamp 102, 104 away from each other, each of the clamps are biased into the open, fixation element receiving position. Likewise, by biasing the forward ends of inner and outer jaws of each clamp 102, 104 toward each other, each of the clamps are biased into a closed, provisionally locked position.

When the block 112 is pressed in towards the middle of the clamp 102, the outer jaw 108 moves to a provisionally locked position. In this position, the biasing element 124 biases the inner and outer jaws 108, 110 together to hold the clamp in the closed position. To pull the fixation element out of the clamp 102 in any direction besides the direction of the long axis of the fixation element, the inner jaw 110 and outer jaw 108 must move apart at their forward ends, where in this exemplary embodiment, they contact the fixation element. In FIG. 2, this can be seen with the jaws 108, 110 and the points 184, 186. In order to accommodate separation of the jaws 108, 110 at their front ends, the back portion of the jaws 108, 110 must move closer together. However, this is prohibited because the block 112 is disposed between the inner and outer jaws 110, 108 in the manner shown in FIGS. 2 and 4. Additionally, force to remove the fixation element would apply loading that would separate the points 184, 186 (FIG. 2), thereby increasing the force on the block 112. This is the case when just spring force of the biasing member 124 biases the inner and outer jaws together. Additional clamping force applied by the locking mechanism 106 formed of the nut 120 and bolt 118 squeezes the fixation element and the block 112 even tighter, preventing a user from opening the clamp 102. Accordingly, the additional clamping force may change the provisionally locked condition, which may permit rotation and some manipulation of the clamp assembly 100 relative to the fixation elements, to a final or fully locked condition lock where the clamp assembly 100 is rigidly fixed in place relative to the fixation elements.

To open the clamp systems 102 the clamping force from the locking assembly 106 is relieved by loosening the nut 120. Once this is loosened enough to provide sufficient travel for the outer jaw 108, the block 112 can be pulled away from the middle of the clamp 102 so that it is no longer between the inner and outer jaws 110, 108, and the outer jaw 108 will rotate to a fixation element receiving position.

Figure 8A:
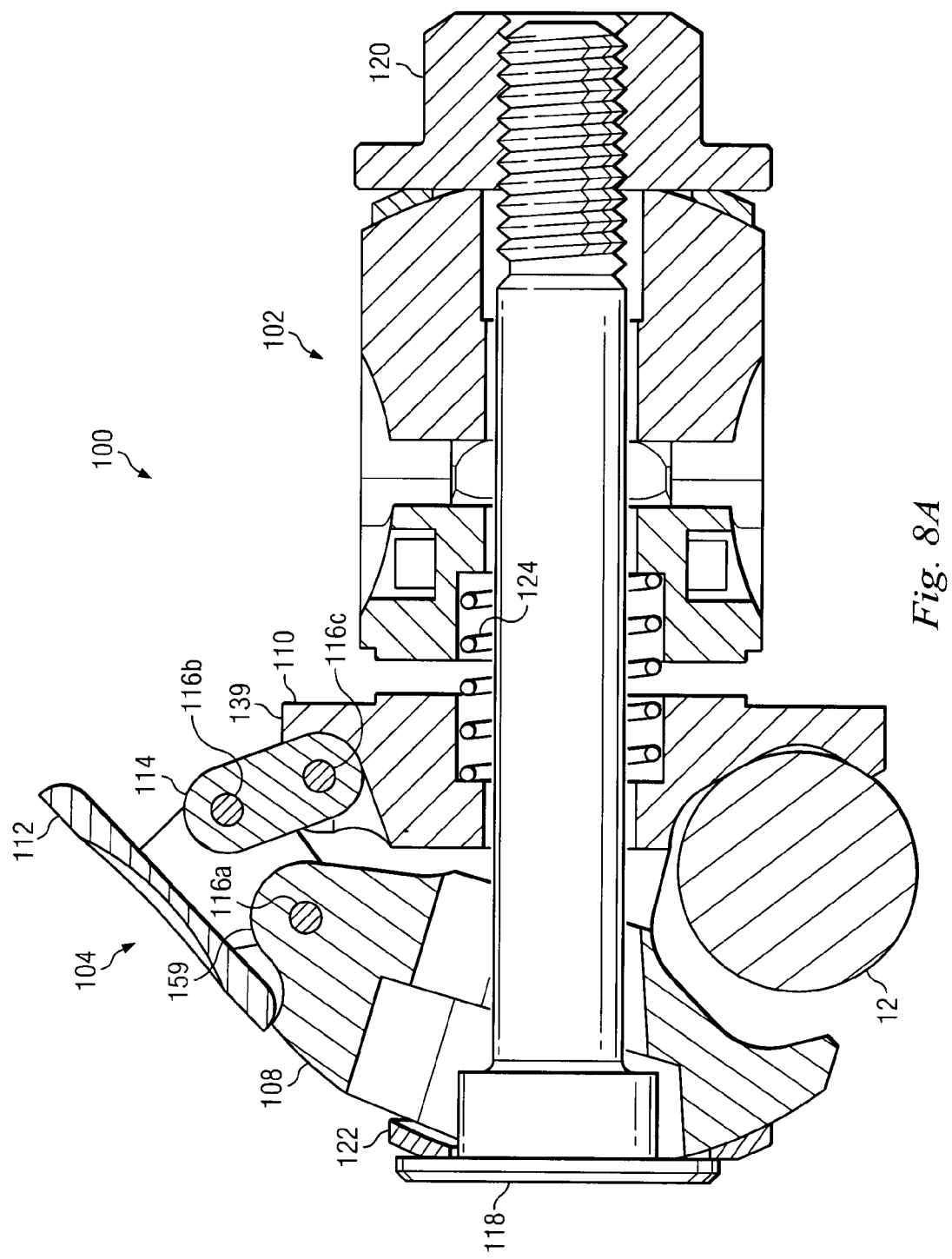
FIGS. 8A-8D are illustrations of cross-sectional views of the clamping assembly in different stages between open and closed according to one exemplary aspect of the present disclosure.
Figure 8B:
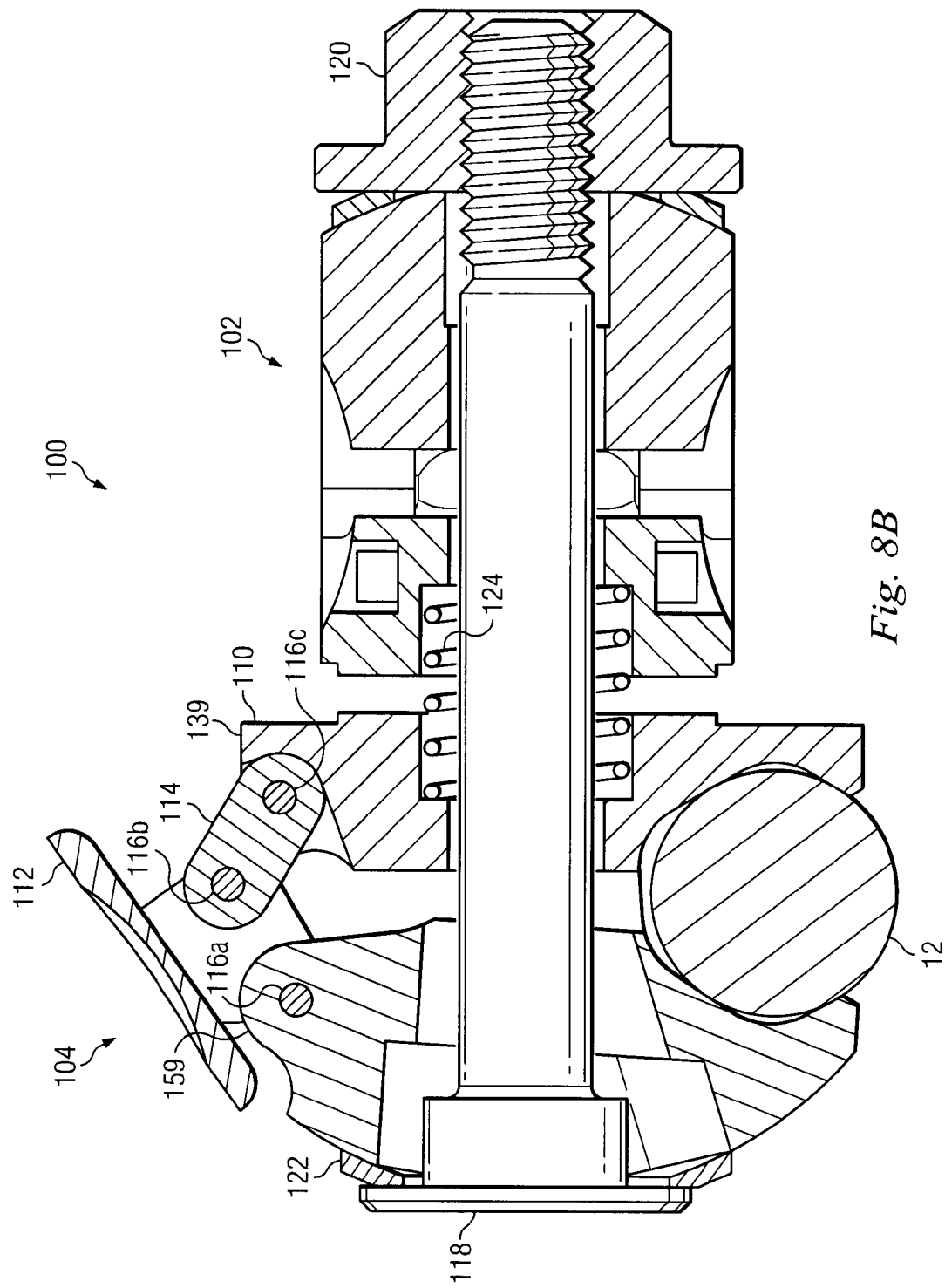
Figure 8C:
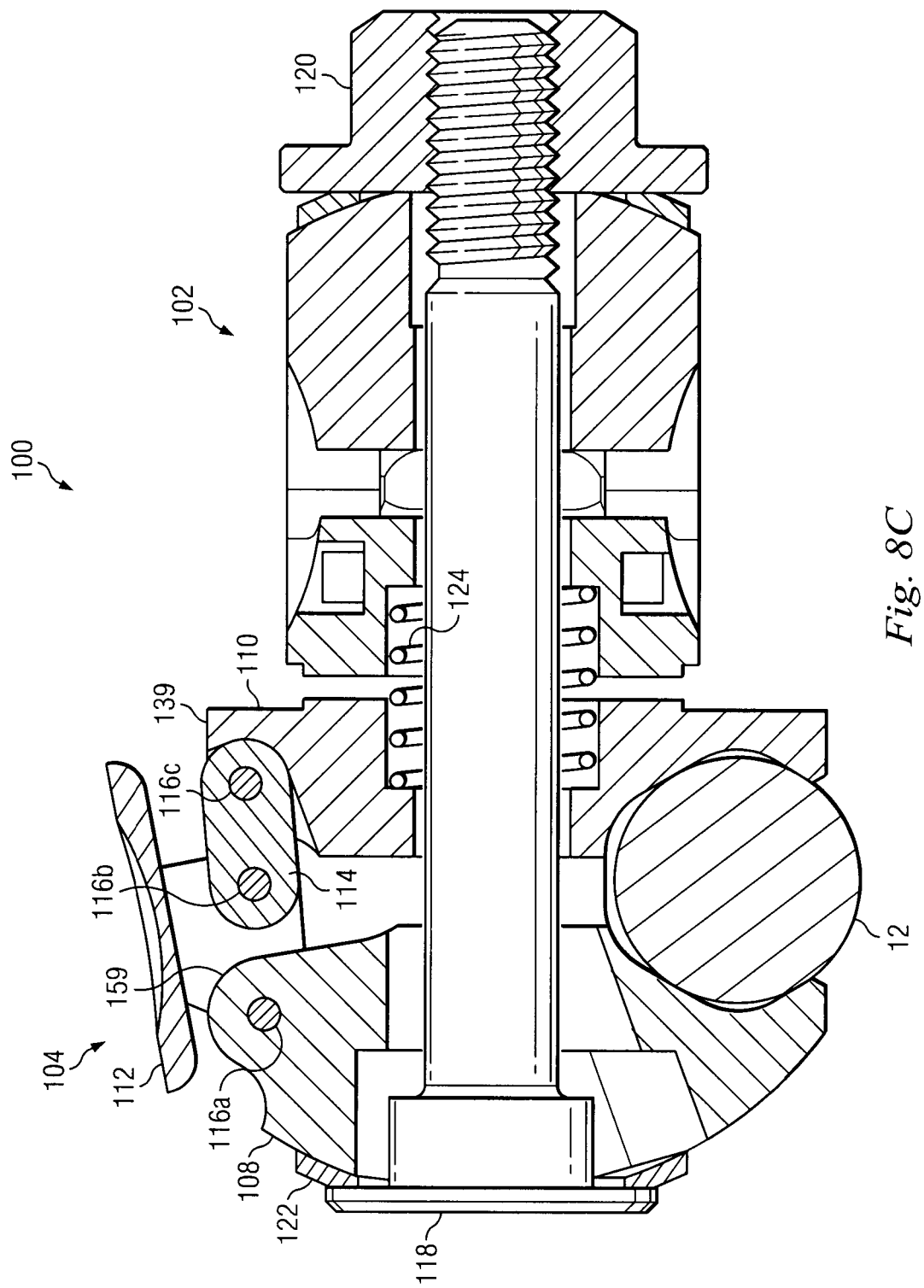
Figure 8D:
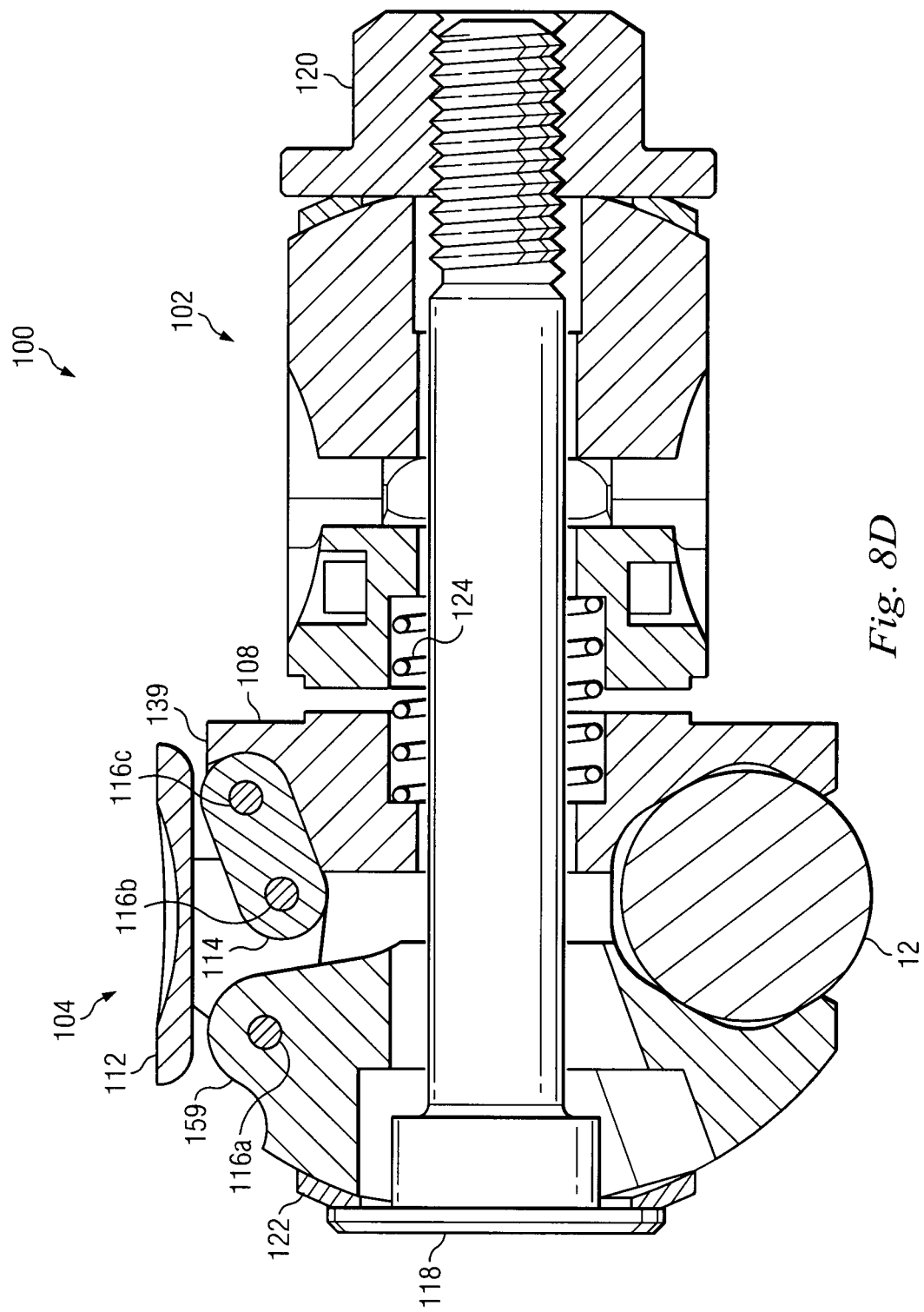
Figure 9:
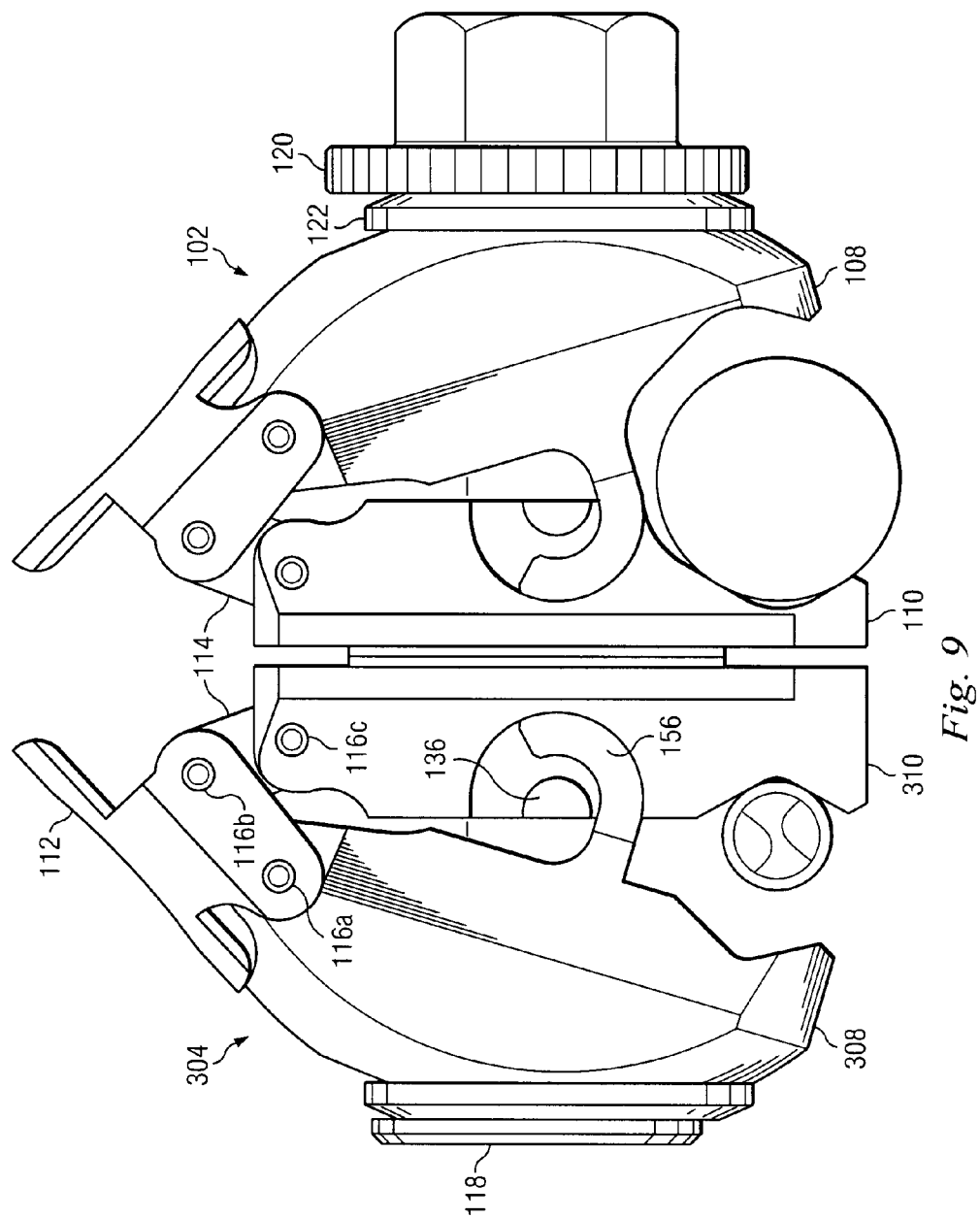
FIG. 9 is an illustration of a side view of a second embodiment of an external fixation system with a clamp assembly having a pin clamp and a rod clamp according to one exemplary aspect of the present disclosure.
Figure 10:
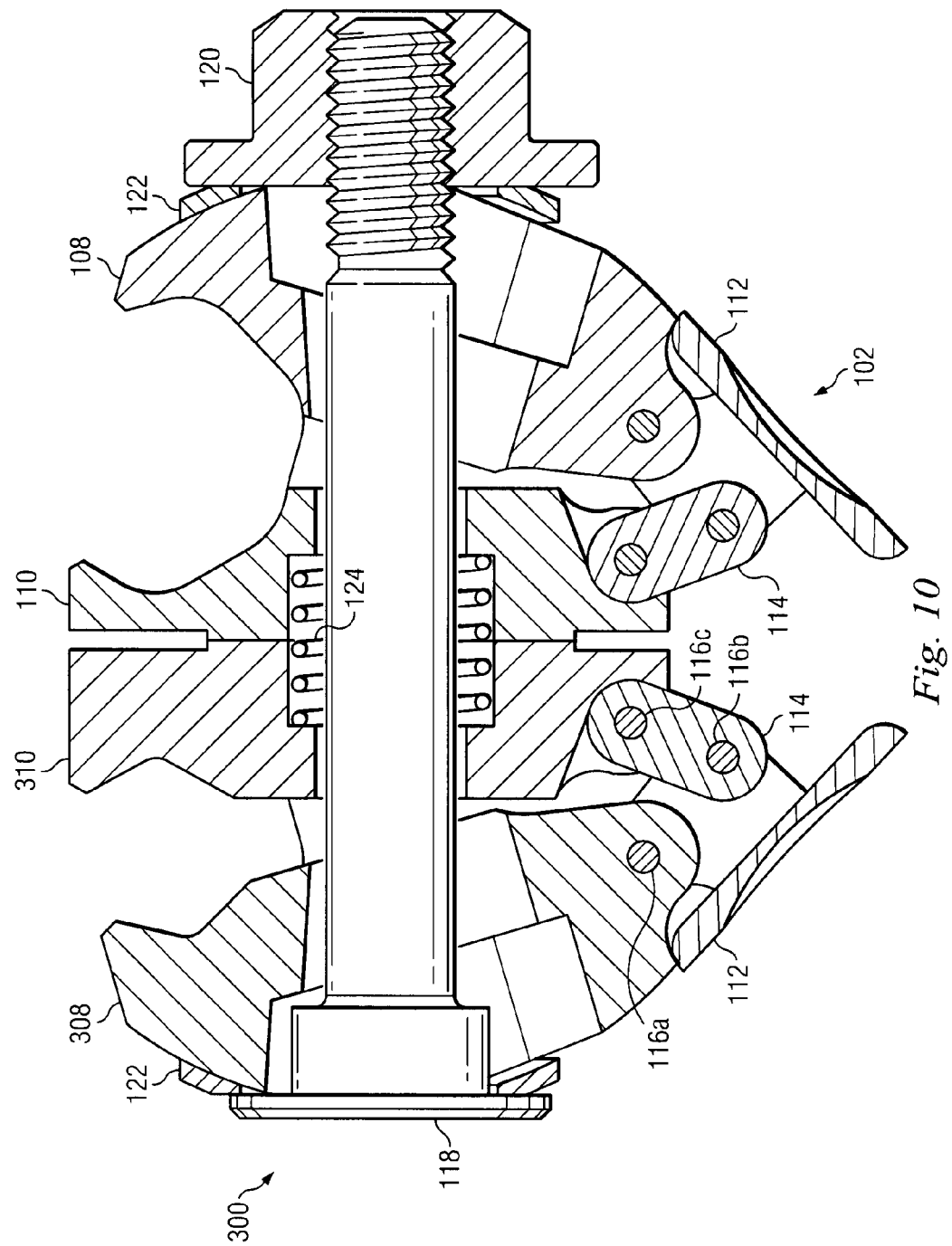
FIG. 10 is a cross-sectional view through the clamping assembly of FIG. 9 showing the pin and rod clamps in the open condition without the fixation elements.
Figure 11:
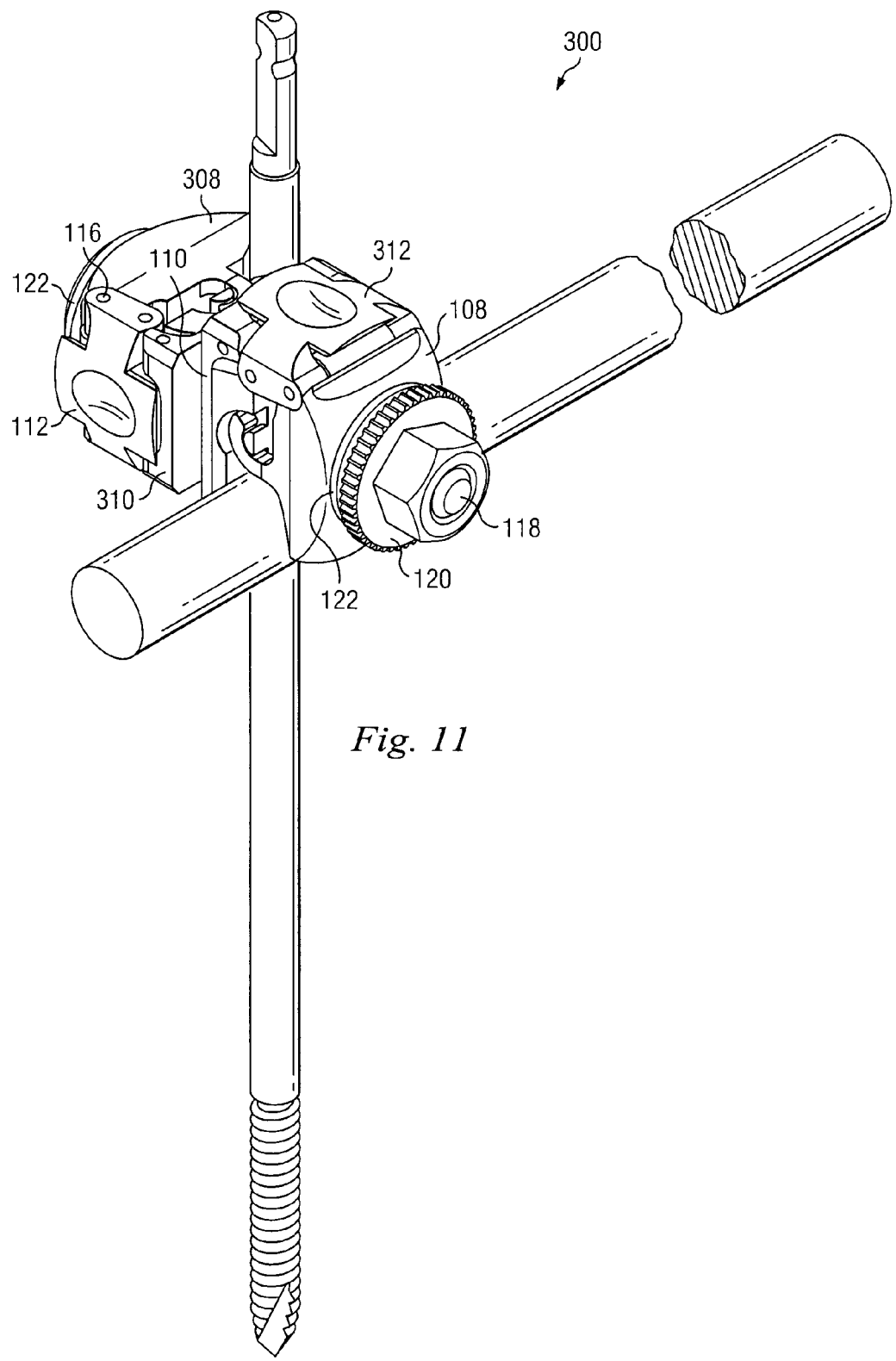
FIG. 11 is an isometric view of a portion of an external fixation system showing one exemplary embodiment of a clamp assembly clamped onto one bar and one bone pin.
Figure 12:
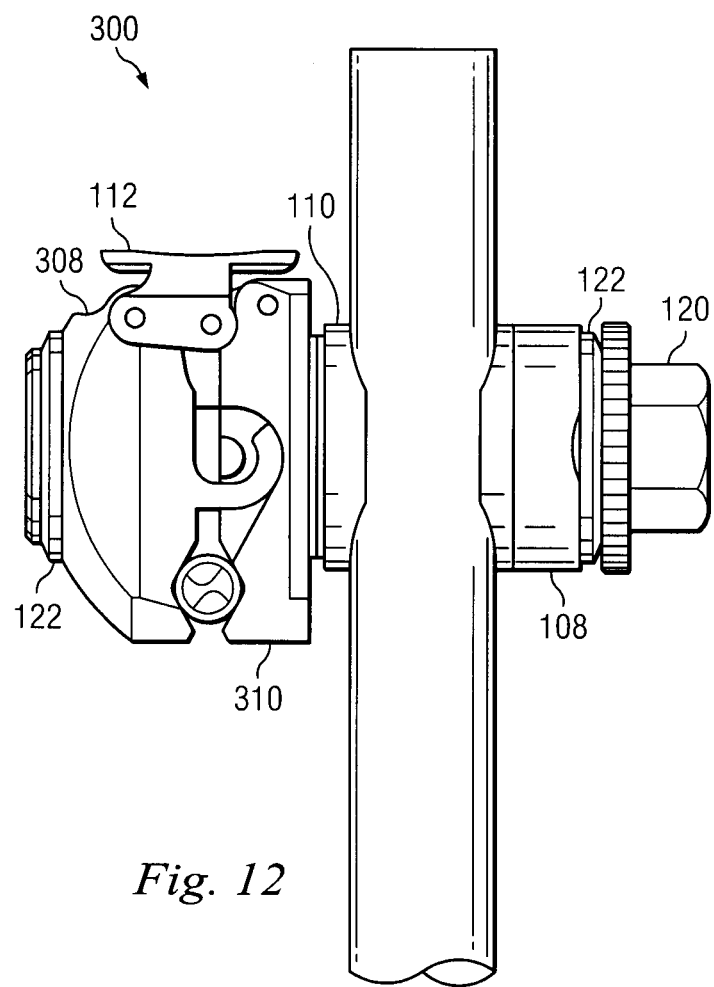
FIG. 12 is a side view of the portion of the external fixation system shown in FIG. 11, showing the exemplary clamp assembly clamped onto one bar and one bone pin.
Figure 12:
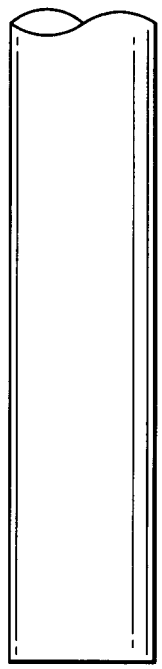

FIGS. 8A-8D show the steps of locking a fixation element in the clamping device 100 in even greater detail. Although operation is the same between clamps, the description below references the clamp 104 rather than the clamp 102. FIG. 8A shows the clamping device 100 with the clamp 104 in an open position. FIG. 8B shows the clamping device 100 with the clamp 104 in the half-open position. FIG. 8C shows the clamping device 100 with the linkage of the clamp 104 in the top-center position. FIG. 8D shows the clamping device 100 with the clamp 104 in the closed, provisionally locked condition. FIG. 2 described above shows the clamping device 100 in the fully locked condition.

Referring first to FIG. 8A, as can be seen and as described above, the link 114 is connected to and pivots about the axle 116a extending into the inner jaw 110, and the block 112 is connected to and pivots about the axle 116c extending into the outer jaw 108. The axle 116b pivotably connects the block 112 and the link 114. As described above, these four elements pivotably connect and form a linkage that can secure the fixation element within the clamp. To place the clamp 104 in position shown in FIG. 8A, the surgeon pulls the tab 174 away from the jaws 108, 110. In this position, a reference line transverse to and passing through the axles 116a, 116b forms an angle with a reference line transverse to and passing through the axles 116b, 116c. As the angle formed between the axles 116a, 116b on the block 112 and the axle 116b, 116c on the link 114 increases, the distance between the rear portions 139, 159 of the outer and inner jaws 108, 110 decreases, and the jaw tips defining an opening to the passage separate further opening the jaws to receive the fixation element. As this occurs, and with reference to FIG. 4, the outer jaw 108 pivots relative to the inner jaw 110 at the connector portions, which in this example includes hooks 156 pivoting about bosses 136 on either side of the clamp 104. The track 134 and cylindrical surface 138 prevent the outer jaw 108 from collapsing onto the inner jaw 110 and maintains the desired separation distance between the jaws 108, 110. Accordingly, the outer jaw 108 pivots relative to the inner jaw 110 about the center of the J-hook. The biasing member 124 biases the empty clamp 104 to the open position when the link 114 and block 112 are in the position shown in FIG. 8A.

FIG. 8B shows the clamp in a half closed position, with the outer and inner jaws 108, 110 together contacting the fixation element 12 on four sides. Accordingly, the fixation element 12 is fixed in place and does not move further into the passage formed between the jaws 108, 110 and does not move out of the passage. Accordingly, the angle formed between the axles 116a, 116b, on the block 112 and the axles 116b, 116c on the link 114 decreases, bringing the axles 116a, 116b, 116c closer to alignment, increasing the distance between the rear portions 139, 159 of the outer and inner jaws 108, 110, and decreasing the distance between the jaw tips. At the same time, the pivot point changes from the J-hook center to the center of the fixation element 12. The biasing member 124 continues to bias the clamp 104 to the open position when the link 114 and block 112 are in the position shown in FIG. 8B. However, since the change in angle forces the rearward end of the jaws 108, 110 apart, this movement correspondingly opposes the biasing force and somewhat compresses the biasing member 124. Accordingly, at this point, the biasing element 124 is still biasing the rearward portion of the inner jaws toward each other, thereby biasing the jaws toward an open position.

FIG. 8C shows the linkage at the top center position with the axles 116a, 116b, and 116c aligned. Accordingly, at this point, the angle has become zero, as the links pass from a from a position forming a positive angle to a position forming a negative angle. With the angle at zero, the links are in a neutral position. At this point, the outer and inner jaws 108, 110 are supported primarily at two locations: at the front of the jaws by the fixation element and the rear portions of the jaws by the block 112 and the link 114. At this point, the biasing element 124 is biasing the inner jaw 108 toward the outer jaw 110, thereby biasing the jaws toward each other to a closed, provisionally locked position. If the linkage moves from the neutral position to a position having a positive angle (away from the center of the clamp), the biasing element 124 will bias the jaws toward an open position by pushing the rear portions together. In contrast, if the linkage moves from the neutral position to a position having a negative angle (toward the center of the clamp), the biasing element 124 will bias the jaws toward a closed, provisionally locked position by pushing the linkage into the position shown in FIG. 8D.

FIG. 8D shows the linkage in its seated, stable position. In this position, the biasing member 124 biases the inner jaw 110 toward the outer jaw 108 in a manner that any applied force to open the jaws would actually drive the linkage, and ultimately the clamp, tighter into the closed position. For example, if the surgeon were to attempt to remove the fixation element 12 from between the outer and inner jaws 108, 110, the force would be transferred to the front of the jaws, which would push the rear portions 139, 159 closer together. Pushing the rear portions 139, 159 closer together results in more tightly compressing the block 112. In this position, as can be seen in FIG. 8D, the link 112 is fully seated in the seat 140 in the inner jaw 110. Likewise, the arm portions 164 of the block 112 are fully seated in the block seat 141 and in the lateral recesses 158. Since the biasing element 124 is biasing the jaws together in FIG. 8D, the chance of inadvertent opening of the clamp is reduced or entirely prevented.

With the clamping device 100 arranged as shown in FIG. 8D, the fixation element 12 is provisionally locked within the clamp 104. Accordingly, the clamp may pivot or slide about the fixation element and the clamp 104 may be rotated relative to the clamp 102 about the bolt 118.

FIG. 3 shows the clamping device 100 in a fully locked condition. The clamping device arrives at this condition when the surgeon tightens the locking mechanism 106, which in this example includes tightening the nut 120 on the bolt 118. This drives the clamps 102, 104 toward each other compressing the biasing element 124. When the clamps 102, 104 contact each other, their respective clamp interfacing portions 148 engage and may prevent relative rotation. For example, interdigitations formed on the inner jaws 110 may engage and prevent relative rotation. At the same time, tightening the locking mechanism 106 further presses the outer and inner jaws 108, 110 together, tightening them down on the fixation element 12 until the fixation element is secured against movement relative to the clamping device 100, rigidly locking the clamping device 100. In this position, the clamping device 100 is in a fully locked condition.

FIGS. 9-12 show a second embodiment of a clamping device, referenced herein by the numeral 300. This embodiment is similar in many respects to the embodiment described above, but includes a pin clamp 304 in combination with the rod clamp 102. In this example the clamping device 300 is a part of a fixation system that may include a bone pin and a fixation rod. Other clamp embodiments are also contemplated, and the surgeon can build a structure to meet the needs of the particular case utilizing bar to bar clamps, bar to pin clamps, bars and bone pins. In this example, the pin clamp 304 includes an outer jaw 308 and an inner jaw 310 that are shaped to receive a bone pin, which typically includes a smaller diameter than a fixation rod. Accordingly, the outer and inner jaws 308, 310 differ in construct to accommodate the bone pin while maintaining all other aspects the same, including the block 112 and the link 114.

The clamping device 300 operates in the same manner described above. That is, a surgeon may use the clamping assembly 300 as a part of an external fixation system to fix a rod to a bone pin or a rod to another rod. With the clamps 102, 304 in the open position shown in FIGS. 9 and 10, the surgeon may introduce the rods or pins into the openings formed between the inner and outer jaws. The surgeon may then manually actuate the block 112 of each respective clamp so that the respective clamp snaps onto or otherwise closes about the rod or pin, to capture the rod or pin. Actuating the block 112 may include pressing the tab 174 on the block 112 so that it pivots about the axles. As the tab 174 is pressed, the block 112 rotates, guided by the links 114 and axles 116, so that an interference portion of the block 112 advances between the rear portions of the inner and outer jaws. As it advances, the rear portion of the outer jaw moves away from the rear portion of the inner jaw, creating a gap therebetween that is filled by the advancing block 112. As the inner and outer jaws move away from each other at the rear portion, the front ends of the jaws move toward each other in manner that captures the rod or pin therebetween.

In this condition, the rod or pin is captured between the inner and outer jaws. However, in this embodiment, the captured rod or pin can be rotated within the jaws and the clamping assembly may be slid in the direction of the rod axis along the rod. To rigidly lock the clamp on the rod or pin, the locking system 106 must be actuated as described above.

As described above, opening the clamp occurs by using the tab 174 to pull the block 112 out from between the inner and outer clamps. The biasing member 124, here shown as a coil spring, biases the jaws open as soon as the block is removed sufficiently from the space between the backs of the jaws.

The foregoing has outlined features of several embodiments. Those skilled in the art should appreciate that they may readily use the present disclosure as a basis for designing or modifying other processes and structures for carrying out the same purposes and/or achieving the same advantages of the embodiments introduced herein. Those skilled in the art should also realize that such equivalent constructions do not depart from the spirit and scope of the present disclosure, and that they may make various changes, substitutions and alterations herein without departing from the spirit and scope of the present disclosure.

I claim:

1. A clamp assembly for an external fixation system, comprising:
   a first jaw comprising a clamping portion and a rear portion opposite the clamping portion;
   a second jaw comprising a clamping portion and a rear portion opposite the clamping portion, the clamping portions of the first and second jaws together forming a passage for receiving a first fixation element of the external fixation system;
   a first link pivotally connected to the rear portion of the first jaw; and
   a second link pivotally connected to the rear portion of the second jaw and to the first link, the first link comprising a first portion pivotally connected to the rear portion of the first jaw and a second portion pivotally connected to the second link, and the first and second links being pivotable between a first position and a second position, wherein:
      in the first position, the first portion of the first link is received in a seat in the rear portion of the first jaw and the second portion of the first link is offset from the rear portion of the second jaw such that the first and second jaws can assume an open position; and
      in the second position, the first portion of the first link is received in the seat in the rear portion of the first jaw and the second portion of the first link is received in a seat in the rear portion of the second jaw such that the first and second jaws can assume a closed position and the first and second portions of the first link resist separation of the jaws.

2. The clamp assembly of claim 1, further comprising a biasing element arranged so as to bias the clamp to the open position when the first and second links are disposed in the first position.

3. The clamp assembly of claim 2, wherein the clamp is arranged so that the biasing element biases the clamp to the closed position when the first and second links are disposed in the second position.

4. The clamp assembly of claim 1, wherein the first jaw includes a first connector portion and wherein the second jaw includes a second connector portion, the first and second jaws being connected at the first and second connector portions.

5. The clamp assembly of claim 4, wherein the first connector portion pivots about the second connector portion.

6. The clamp assembly of claim 4, wherein the first connector portion is a J-hook and the second connector portion is a boss, the J-hook extending about the boss.

7. The clamp assembly of claim 4, wherein the first connector portion is sized relative to the second connector portion to allow a limited amount of travel of the first jaw relative to the second jaw.

8. The clamp assembly of claim 1, wherein the first link comprises first and second arm portions and a back portion connecting the first and second arm portions, the second link being disposable between the first and second arm portions.

9. The clamp assembly of claim 8,
wherein the first arm portion comprises first and second ends and the second arm portion comprises first and second ends, and
wherein:
in the first position, the first end of the first arm portion is received in a first seat in the rear portion of the first jaw, the first end of the second arm portion is received in a second seat in the rear portion of the first jaw, and the second ends of the first and second arm portions are offset from the rear portion of the second jaw such that the first and second jaws can assume the open position; and
in the second position, the first end of the first arm portion is received in the first seat in the rear portion of the first jaw, the first end of the second arm portion is received in the second seat in the rear portion of the first jaw, the second end of the first arm portion is received in a third seat in the rear portion of the second jaw, and the second end of the second arm portion is received in a fourth seat in the rear portion of the second jaw such that the first and second jaws can assume the closed position and the first and second arm portions resist separation of the jaws.

10. The clamp assembly of claim 1, wherein the first jaw is connected to the first link via a first axle and wherein the second jaw is connected to the second link via a second axle and wherein the first and second links are connected via a third axle.

11. The clamp assembly of claim 1, wherein the first and second links are arranged to pivot from the first position forming a positive angle between the first and second links to the second position forming a negative angle between the first and second links.

12. An external fixation system, comprising:
a first fixation element;
a second fixation element;
a first clamp configured to capture the first fixation element between clamping portions of first and second jaws of the first clamp, the first clamp comprising a first linkage pivotally connected to rear portions of the first and second jaws and comprising:
a first link; and
a second link pivotally connected to the rear portion of the second jaw and a to the first link, the first link comprising a first portion pivotally connected to the rear portion of the first jaw and a second portion pivotally connected to the second link, and the first and second links being pivotable between a first position and a second position, wherein:
in the first position, the first portion of the first link is received in a seat in the rear portion of the first jaw and the second portion of the first link is offset from the rear portion of the second jaw such that the first and second jaws can assume an open position; and
in the second position, the first portion of the first link is received in the seat in the rear portion of the first jaw and the second portion of the first link is received in a seat in the rear portion of the second jaw such that the first and second jaws can assume a closed position and the first and second portions of the first link resist separation of the first and second jaws; and
a second clamp pivotable relative to the first clamp and configured to capture the second fixation element, the second clamp having a second linkage comprising third and fourth links that are able to be actuated to open the second clamp.

13. The system of claim 12, further comprising a biasing element separating the first and second clamps, the first clamp being arranged so that the biasing element biases the clamp to the open position when the first and second links are disposed in the first position.

14. The system of claim 13, wherein the first clamp is arranged so that the biasing element biases the clamp to the closed position when the first and second links are disposed in the first position.

15. The system of claim 12, wherein the first jaw comprises a first connector portion, and the second jaw comprises a second connector portion, the first connector portion pivoting about the second connector portion.

16. The clamp assembly of claim 15, wherein the first connector portion is sized relative to the second connector portion to allow a limited amount of travel of the first jaw relative to the second jaw.

17. The system of claim 15, wherein the first connector portion is a J-hook and the second connector portion is a boss, the J-hook being pivotable about the boss.

18. The system of claim 12, wherein the first link comprises first and second arm portions and a back portion connecting the first and second arm portions, the second link being disposable between the first and second arm portions.

19. The system of claim 18,
wherein the first arm portion comprises first and second ends and the second arm portion comprises first and second ends, and
wherein:
in the first position, the first end of the first arm portion is received in a first seat in the rear portion of the first jaw, the first end of the second arm portion is received in a second seat in the rear portion of the first jaw, and the second ends of the first and second arm portions are offset from the rear portion of the second jaw such that the first and second jaws can assume the open position; and
in the second position, the first end of the first arm portion is received in the first seat in the rear portion of the first jaw, the first end of the second arm portion is received in the second seat in the rear portion of the first jaw, the second end of the first arm portion is received in a third seat in the rear portion of the second jaw, and the second end of the second arm portion is received in a fourth seat in the rear portion of the second jaw such that the first and second jaws can assume the closed position and the first and second arm portions resist separation of the jaws.

20. A method of clamping a fixation element in an external fixation clamp, comprising:
  inserting the fixation element into a passage formed between clamping portions of first and second jaws of the clamp;
  moving a linkage between a first position and a second position to pivot the first jaw relative to the second jaw, the linkage comprising:
    a first link; and
    a second link pivotally connected to a rear portion of the second jaw and to the first link, the first link comprising a first portion pivotally connected to a rear portion of the first jaw and a second portion pivotally connected to the second link,
  wherein moving the linkage between the first position and the second position comprises:
    moving the first link to cause the first portion to pivot relative to the rear portion of the first jaw and to cause the second portion to move toward and be received in a seat in the rear portion of the second jaw.

21. The method of claim 20, comprising tightening a locking mechanism to render the clamp in a locked position to rigidly secure the fixation element in the clamp.

* * * * *